(12) United States Patent
Tzeng et al.

(10) Patent No.: US 8,273,760 B2
(45) Date of Patent: *Sep. 25, 2012

(54) INDOLO[3,2-C]QUINOLINE COMPOUNDS

(75) Inventors: Cherng-Chyi Tzeng, Kaohsiung (TW); Yeh-Long Chen, Kaohsiung (TW); Jing-Jer Lin, Taipei (TW); Chih-Ming Lu, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 282 days.

This patent is subject to a terminal disclaimer.

(21) Appl. No.: 12/551,315

(22) Filed: Aug. 31, 2009

(65) Prior Publication Data

US 2010/0286163 A1     Nov. 11, 2010

Related U.S. Application Data

(63) Continuation-in-part of application No. 12/421,193, filed on Apr. 9, 2009, now Pat. No. 7,763,633.

(60) Provisional application No. 61/043,907, filed on Apr. 10, 2008.

(51) Int. Cl.
    *A61K 31/4745*     (2006.01)
    *A61K 31/496*     (2006.01)
    *C07D 471/06*     (2006.01)
    *C07D 403/06*     (2006.01)

(52) U.S. Cl. ........... 514/285; 546/70; 544/361; 514/253

(58) Field of Classification Search .................. 514/285, 514/253; 546/70; 544/361
See application file for complete search history.

(56) References Cited

U.S. PATENT DOCUMENTS 7,763,633 B2 *   7/2010   Tzeng et al. .................. 514/285

FOREIGN PATENT DOCUMENTS

EP     226508     12/1986

OTHER PUBLICATIONS

Molina, et al., "New Methodology for the preparation of Pyrrole and Indole Derivatives Via Iminophosphoranes: Synthesis of Pyrrolo[I,2-a] QuinoXalines, Indolo[3,2-c] Quinolines and Indolo[1,2-c] Quinazolines", Tetrahedron vol. 46, No. 3. pp. 1063-1078, 1990.

* cited by examiner

*Primary Examiner* — Charanjit Aulakh
(74) *Attorney, Agent, or Firm* — Occhiuti Rohlicek & Tsao LLP

(57) ABSTRACT

Disclosed herein are indolo[3,2-c]quinoline compounds of formula (I):

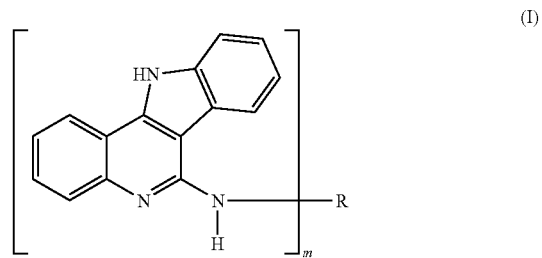

or a pharmaceutically acceptable salt thereof,
wherein R and m are given the definitions as set forth in the Specification and Claims.
These compounds can be used to inhibit both growth of cancer cells and activity of telomerase.

8 Claims, 1 Drawing Sheet

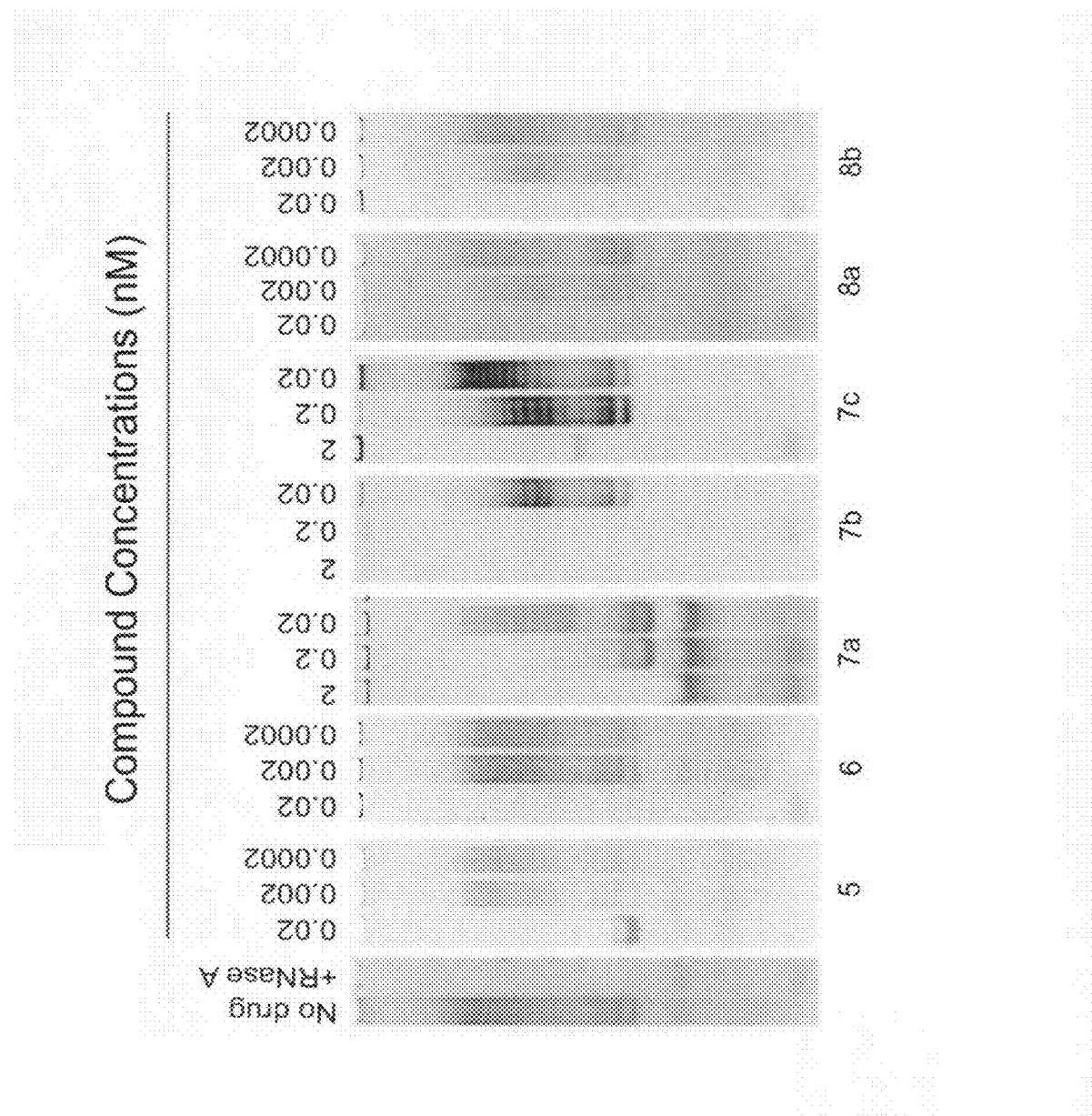

INDOLO[3,2-C]QUINOLINE COMPOUNDS

CROSS-REFERENCE TO RELATED APPLICATION

This application is a continuation-in-part application of U.S. patent application Ser. No. 12/421,193 filed on Apr. 9, 2009 now U.S. Pat. No. 7,763,633, entitled "Indolo[3,2-c]quinoline Compounds," the content of which is incorporated herein by reference in its entirety.

Application Ser. No. 12/421,193 claims the benefit of Provisional Patent Application No. 61/043,907 filed on Apr. 10, 2008, entitled "Indolo[3,2-c]quinoline Compounds," the content of which is also incorporated herein by reference in its entirety.

BACKGROUND OF THE INVENTION

1. Field of the Invention

This invention relates to novel indolo[3,2-c]quinoline compounds, which have been proven to inhibit both growth of a variety of cancer cells and activity of telomerase, a common target for treating cancer. This invention also relates to the applications of said compounds in the manufacture of pharmaceutical compositions.

2. Description of the Related Art

Ever since isocryptolepine, one of the indolo[3,2-c]quinoline-type alkaloids, was isolated from *Cryptoleptis sanguinolenta* (a plant used in traditional medicine against malaria), several indolo[3,2-c]quinoline compounds have been synthesized and extensively studied as potential antiplasmodial agents. See, e.g., Timari, G. et al., *Synlett.* 1997, 1067; Devaraj, R. et al., *Bioorg. Med. Chem. Lett.* 1997, 7, 369; Xiao, Z. et al., *Bioorg. Med. Chem.* 2001, 11, 2875-2878; Kumar, R. N. et al., *Tetrahedron Lett.* 2002, 43, 3327; Mulwad, V. V. et al., *Indian J. Chem. Section B,* 2003, 42B, 1937; and Miert, S. V. et al., *J. Nat. Prod.* 2005, 68, 674-677. Some indolo[3,2-c]quinoline compounds were prepared and evaluated for anticancer effects. See, e.g., Chen, Y. L. et al., *Bioorg. Med. Chem.* 2002, 10, 2705; Lin, Y. H. et al., *Drug Dev. Res.* 2006, 67, 743; and Hu, X. W. et al., *Cell Biol. Toxicol.* 2006, 22, 417. Indolo[3,2-c]quinoline compounds have a tetracyclic heterocycle that can intercalate into the double helix of DNA to block DNA replication or transcription, resulting in inhibition of tumor cell growth. See, e.g., Molina, A, et al., *J. Org. Chem.* 1996, 61, 5587.

EP 0226508 A1 discloses indolo[3,2-c]quinoline derivatives of the following formula (I):

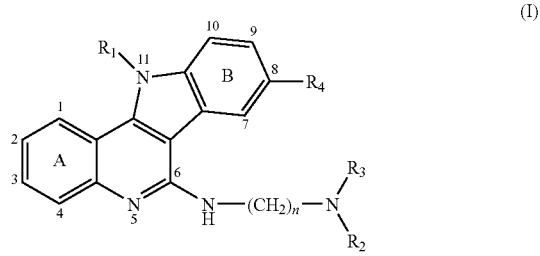

(I)

in which n denotes an integer from 2 to 4, $R_1$ denotes hydrogen or a lower alkyl group, $R_2$ and $R_3$ denote hydrogen or a lower alkyl group, or else $R_2$ and $R_3$ form together and with the nitrogen atom to which they are attached a saturated heterocyclic ring which may contain a second heteroatom such as oxygen, sulfur or nitrogen, and $R_4$ denotes a hydroxyl group or a lower alkoxy group;

and their addition salts with pharmaceutically acceptable inorganic or organic acids and the tautomeric forms when they exist.

In previous studies, the applicants synthesized several N-substituted 11H-indolo[3,2-c]quinolin-6-amines and evaluated the same in vitro against a full panel of 60 human tumor cell lines derived from nine cancer cell types at the US National Cancer Institute (NCI), amongst which N'-(11H-indolo[3,2-c]quinolin-6-yl)-N,N-dimethyl-ethane-1,2-diamine (IQDMA) was observed to exhibit potential anticancer effects against human leukemia HL-60 cells with 50% cell growth inhibition ($GI_{50}$) of 1.98 μM (Yeh-Long Chen et al. (2002), *Bioorganic & Medicinal Chemistry,* 10:2705-2712; Yi-Hsiung Lin et al. (2006), *Drug development research,* 67:743-751; and Xiu-Wei Hu et al. (2006), *Cell Biol. Toxicol.* 22:414-427).

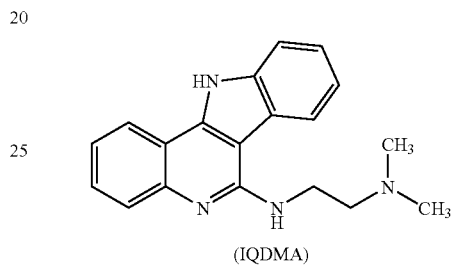

(IQDMA)

In spite of the aforesaid, for pharmachemists and manufacturers in the Pharmaceutical Industry, there still exists a need to develop new compounds that can be easily prepared and that are suitable for use in the treatment of a variety of cancers and tumors.

SUMMARY OF THE INVENTION

Therefore, according to a first aspect, this invention provides a compound of formula (I):

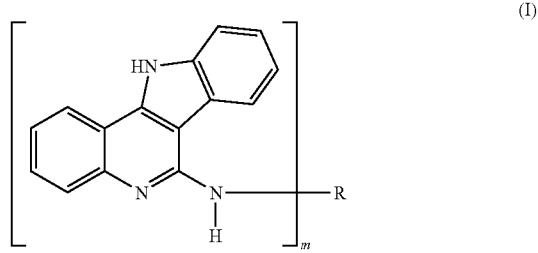

(I)

or a pharmaceutically acceptable salt thereof,
wherein:
m is an integer selected from 1 and 2;
when m is 1, R represents a monovalent group selected from the group consisting of:

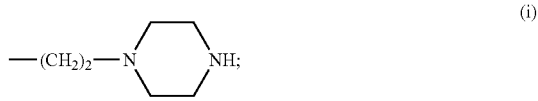

(i)

3

-continued

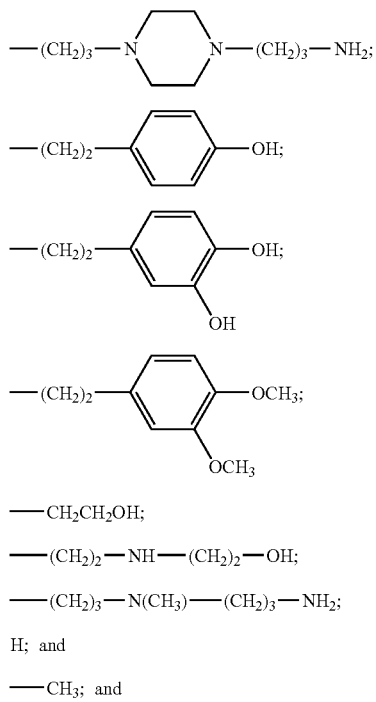

—CH₂CH₂OH;   (vi)

—(CH₂)₂—NH—(CH₂)₂—OH;   (vii)

—(CH₂)₃—N(CH₃)—(CH₂)₃—NH₂;   (viii)

H; and   (ix)

—CH₃; and   (x)

when m is 2, R is a divalent group represented by the formula —(CH₂)$_n$—N(R')—(CH₂)$_n$—, wherein R' is selected from hydrogen and methyl and n is an integer from 2 to 4.

In a second aspect, this invention provides a method of inhibiting DNA replication or transcription in a tumor cell. The method includes contacting the tumor cell with a compound of formula (I) or a pharmaceutically acceptable salt thereof as described above.

In a third aspect, this invention provides a method for treating cancer. The method includes administering to a subject in need thereof a compound of formula (I) or a pharmaceutically acceptable salt thereof as described above.

In a fourth aspect, this invention provides a pharmaceutical composition comprising a compound of formula (I) or a pharmaceutically acceptable salt thereof as described above.

BRIEF DESCRIPTION OF THE DRAWINGS

The above and other objects, features and advantages of this invention will become apparent with reference to the following detailed description and the preferred embodiments taken in conjunction with the accompanying drawing, in which:

FIG. 1 shows the telomerase-inhibitory activities of some selected compounds according to this invention as assessed using a TRAP assay, in which total cell extract (0.5 μg) from H1299 human lung cancer cells was treated with various concentrations (2, 0.2, 0.02, 0.002, and 0.0002 nM) of the selected compounds, followed by telomerase extension, telomerase inactivation and a three-step PCR. The telomerase-extended PCR products were resolved by gel electrophoresis and visualized by staining with SYBER Green. The lane marked with "No drug" represents total cell extract only, which acts as a positive control, and the lane marked with "+RNase A" represents total cell extract treated with 1 μg of RNase A at 37° C. for 30 min, which acts as a negative control.

DETAILED DESCRIPTION OF THE INVENTION

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which this invention belongs. One skilled in the art will recognize many methods and materials similar or equivalent to those described herein, which could be used in the practice of the present invention. Indeed, the present invention is in no way limited to the methods and materials described.

This invention provides novel indolo[3,2-c]quinoline compounds of formula (I):

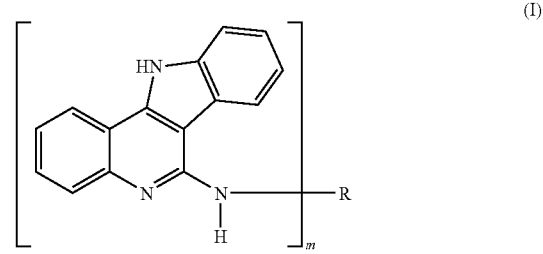

(I)

or a pharmaceutically acceptable salt thereof,
wherein:
m is an integer selected from 1 and 2;
when m is 1, R represents a monovalent group selected from the group consisting of:

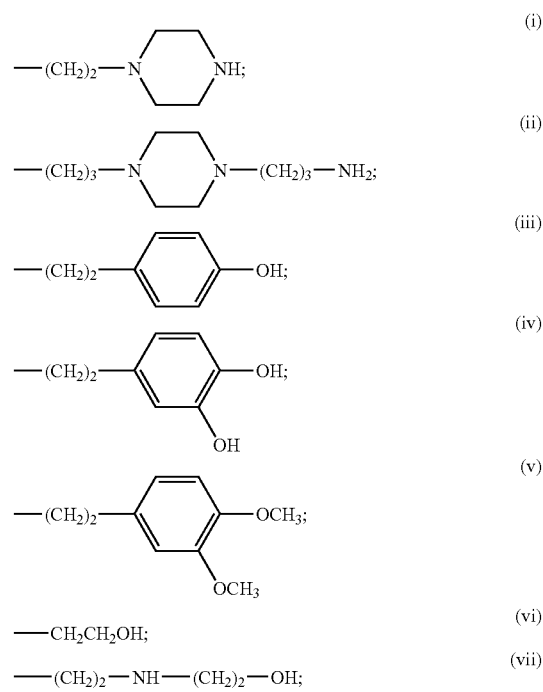

—CH₂CH₂OH;   (vi)

—(CH₂)₂—NH—(CH₂)₂—OH;   (vii)

-continued

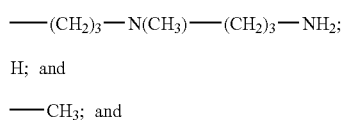

when m is 2, R is a divalent group represented by the formula —(CH$_2$)$_n$—N(R')—(CH$_2$)$_n$—, wherein R' is selected from hydrogen and methyl and n is an integer from 2 to 4.

The term "compound" as used herein refers to both compounds and ions. For example, when —NH— on the quinoline side chain is replaced by —NH$_2$'—, the compound of formula (I) is a cation.

Unless otherwise indicated, the term "monovalent group" as used herein refers to a group having one and only one valency available for binding and does not imply a specific type of binding.

Unless otherwise indicated, the term "divalent group" as used herein refers to a linkage group linking two entities by covalent bonds, in which the linkage group is linked to each of these entities via a single bond.

According to this invention, the indolo[3,2-c]quinoline compounds of formula (I) as described above may be synthesized by the reaction of a compound of formula (II) with an amine compound of either formula R—NH$_2$ or formula H$_2$N—R—NH$_2$:

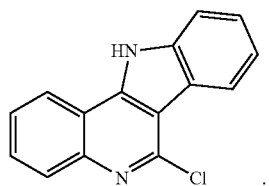

When the amine compound is of the formula R—NH$_2$, the reaction gives rise to a compound of formula (IA):

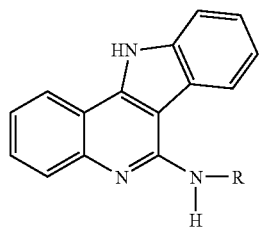

wherein R is the same as that defined for formula (I) described above.

Representative examples of the compound of formula (IA) according to this invention include, but are not limited to:
N-(11H-Indolo[3,2-c]quinolin-6-yl)-2-(piperazin-1-yl)ethanamine;
{3-[4-(3-aminopropyl)piperazin-1-yl]propyl}(11H-indolo[3,2-c]quinolin-6-yl)amine hydrochloride;
6-[2-(4-Hydroxyphenyl)ethylamino]-11H-indolo[3,2-c]quinoline hydrochloride;
6-[2-(3,4-dihydroxyphenyl)ethylamino]-11H-indolo[3,2-c]quinoline hydrochloride;
6-[2-(3,4-dimethoxyphenyl)ethylamino]-11H-indolo[3,2-c]quinoline hydrochloride;
2-(11H-indolo[3,2-c]quinolin-6-ylamino)ethanol hydrochloride;
11H-Indolo[3,2-c]quinolin-6-ylamine hydrochloride;
2-[2-(11H-Indolo[3,2-c]quinolin-6-ylamino)ethylamino]ethanol hydrochloride; and
N$^1$-[3-(11H-indolo[3,2-c]quinolin-6-ylamino)propyl]-N$^1$-methylpropane-1,3-diamine hydrochloride;

When the amine compound is of the formula H$_2$N—R—NH$_2$, the reaction gives rise to a compound of formula (IB):

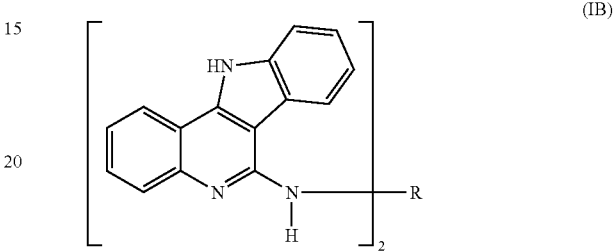

wherein R is the same as that defined for formula (I) described above.

Representative examples of the compound of formula (IB) according to this invention include, but are not limited to:
N,N-bis-[3-(11H-indolo[3,2-c]quinolin-6-yl)aminopropyl]amine hydrochloride; and
N,N-bis-[3-(11H-indolo[3,2-c]quinolin-6-yl)aminopropyl]-N-methylamine hydrochloride.

The compound of formula (II) may be obtained by reacting a compound of formula (III) with POCl$_3$:

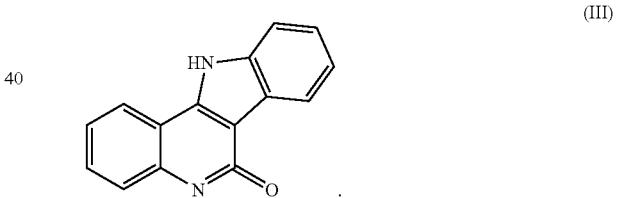

Said compound of formula (III) can be prepared from the reaction of an isatin of formula (IV) and 2-aminobenzylamine:

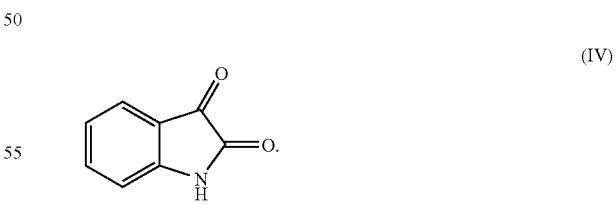

The indolo[3,2-c]quinoline compounds as described above can be prepared by methods well known in the art. An indolo[3,2-c]quinoline compound synthesized above can be purified by a suitable method such as column chromatography, high-pressure liquid chromatography, or recrystallization.

Other indolo[3,2-c]quinoline compounds can be prepared using other suitable starting materials through the above synthesis routes and others known in the art. The methods described above may also additionally include steps, either before or after the steps described specifically herein, to add or remove suitable protecting groups in order to ultimately allow synthesis of the indolo[3,2-c]quinoline compounds. In addition, various synthetic steps may be performed in an alternate sequence or order to give the desired compounds. Synthesis chemistry transformations and protecting group methodologies (protection and deprotection) useful in synthesizing applicable indolo[3,2-c]quinoline compounds are known in the art and include, for example, those described in R. Larock, *Comprehensive Organic Transformations*, VCH Publishers (1989); T. W. Greene and P. G. M. Wuts, *Protective Groups in Organic Synthesis,* 2nd Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The indolo[3,2-c]quinoline compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The compounds of formula (I) according to this invention have been proven to possess excellent activity against the growth of cancer cells, in particular leukemia, non-small cell lung cancer, colon cancer, CNS cancer, melanoma, ovarian cancer, renal cancer, prostate cancer, and breast cancer. These compounds have been further demonstrated to possess ability to inhibit telomerase, suggesting that the compounds of formula (I) according to this invention may exhibit anticancer activity by inhibition upon telomerase. It is thus contemplated that the compounds of formula (I) according to this invention can be used in the treatment of cancer diseases in a subject, including human and other mammals.

Therefore, this invention provides a method for inhibiting DNA replication or transcription in a tumor cell, the method comprising contacting the tumor cell with a compound of formula (I) as described above. The tumor cell is one derived from a cancer selected from leukemia, non-small cell lung cancer, colon cancer, CNS cancer, melanoma, ovarian cancer, renal cancer, prostate cancer, and breast cancer.

Also within the scope of this invention is a method for treating cancer. The method includes administering to a subject in need thereof an indolo[3,2-c]quinoline compound of formula (I) as described above. Examples of cancer that can be treated by the indolo[3,2-c]quinoline compounds of this invention include but are not limited to leukemia, non-small cell lung cancer, colon cancer, CNS cancer, melanoma, ovarian cancer, renal cancer, prostate cancer, and breast cancer. The term "treating" or "treatment" as used herein refers to administering one or more indolo[3,2-c]quinoline compounds of this invention to a subject, who has one of the above-described diseases, a symptom of or a predisposition toward such a disease, with the purpose to confer a therapeutic effect, e.g., to cure, relieve, alter, affect, or ameliorate the disease.

In addition, this invention features a pharmaceutical composition that contains at least one of the above-mentioned indolo[3,2-c]quinoline compounds for use in treating cancer, as well as this therapeutic use and use of the compounds for the manufacture of a medicament for the just-mentioned treatment.

The indolo[3,2-c]quinoline compounds described above include the compounds themselves, as well as their salts, prodrugs, and solvates, if applicable. A salt, for example, can be formed between an anion and a positively charged group (e.g., amino) on an indolo[3,2-c]quinoline compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on an indolo[3,2-c]quinoline compound. Suitable cations include sodium ion, potassium ion, magnesium ion, calcium ion, and an ammonium cation such as tetramethylammonium ion. The indolo[3,2-c]quinoline compounds also include those salts containing quaternary nitrogen atoms. Examples of prodrugs include esters and other pharmaceutically acceptable compounds, which, upon administration to a subject, are capable of providing active indolo[3,2-c]quinoline compounds. A solvate refers to a complex formed between an active indolo[3,2-c]quinoline compound and a pharmaceutically acceptable solvent. Examples of pharmaceutically acceptable solvents include water, ethanol, isopropanol, ethyl acetate, acetic acid, and ethanolamine.

Also within the scope of this invention is a pharmaceutical composition containing at least one indolo[3,2-c]quinoline compound described above and a pharmaceutical acceptable carrier. Further, this invention covers a method of administering an effective amount of one or more of the indolo[3,2-c]quinoline compounds to a patient having cancer. "Effective amount" refers to the amount of an active indolo[3,2-c]quinoline compound that is required to confer a therapeutic effect on the treated subject. Effective doses will vary, as recognized by those skilled in the art, depending on the types of diseases treated, route of administration, excipient usage, and the possibility of co-usage with other therapeutic treatments.

To practice the method of the present invention, a composition having one or more indolo[3,2-d]quinoline compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active indolo[3,2-c]quinoline compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active indolo[3,2-c]quinoline compound. Examples of other carriers include colloidal silicon oxide, magnesium stearate, cellulose, sodium lauryl sulfate, and D&C Yellow #10.

The indolo[3,2-c]quinoline compounds described above can be preliminarily screened for their efficacy in treating above-described diseases by in vitro assays (see Pharmacological Examples below) and then confirmed by clinical trials. Other methods will also be apparent to those of ordinary skill in the art.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

EXAMPLES

The present invention will be described in more detail with reference to the following examples, which are given for the purpose of illustration only and are not intended to limit the scope of the present invention.

The compounds of formula (I) according to this invention can be prepared according to the following reaction scheme and protocols.

Specifically, as shown in Scheme 1, reaction of isatin (1) and 2-aminobenzylamine (2) gives 5,11-dihydro-indolo[3,2-c]quinolin-6-one (3), which may be treated with $POCl_3$ to yield 6-chloro-11H-indolo[3,2-c]quinoline (4), which may be further reacted with either an amine of formula R—$NH_2$ or a diamine of formula $H_2N$—R—$NH_2$ to give a corresponding compound of either formula (IA) or formula (IB).

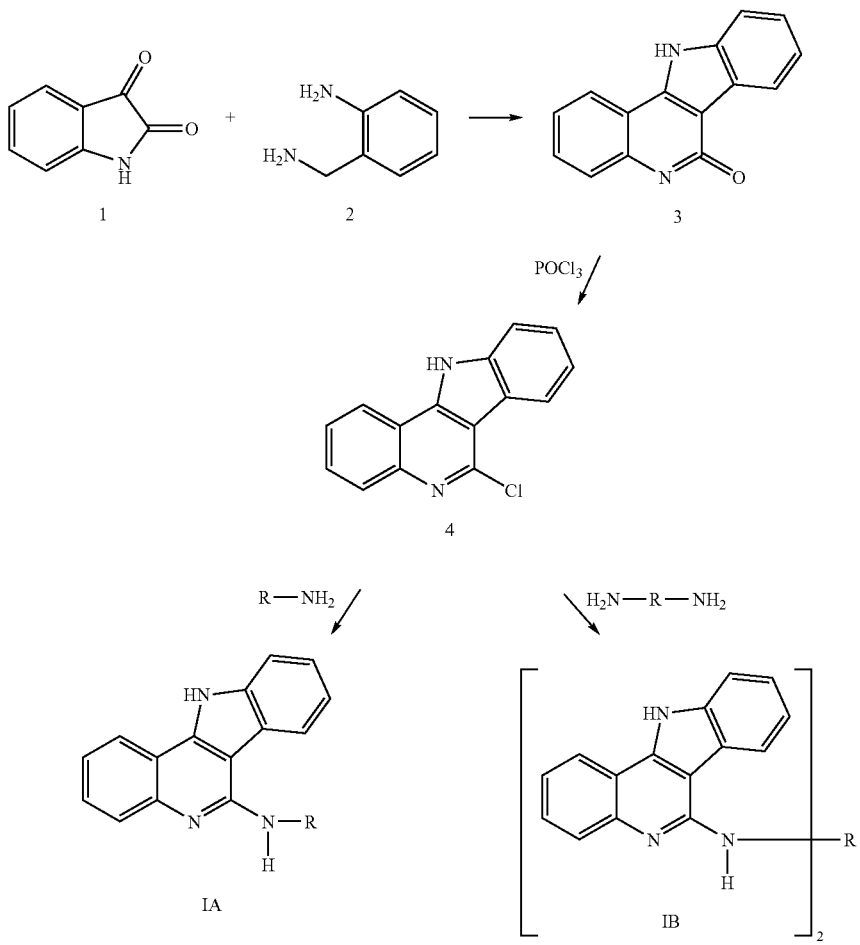

General Procedures:

The melting point of each of the compounds synthesized in the following examples was detected by an uncorrected Electrothermal IA9100 digital melting-point apparatus.

The general thin layer chromatography (TLC) was performed using pre-coated (0.2 mm) silica gel 60 $F_{254}$ plates (EM Laboratories, Inc.), and detected using a UV light at 254 nm.

IR spectra were determined using a Nicolet Magna-IR 550 infrared spectrophotometer.

UV spectra were determined using a Hitachi U-3210 spectrophotometer.

$^1$H-NMR and $^{13}$C-NMR spectra were detected using a Varian-Unity-400 at 100 and 400 MH$_z$, respectively, with chemical shifts being represented by δ in ppm using SiMe$_4$ (=0 ppm) as an internal standard, and coupling constants being represented by J in Hz.

Elemental analyses were carried out on a Heraeus CHN—O-Rapid elemental analyzer, and results were within ±0.4% of calc. values.

Representative compounds of formula (I) according to this invention and their synthetic precursors are shown in the following Table 1.

TABLE 1

The structures of representative compounds of either formula (IA) or (IB) according to this invention and their synthetic precursors

| Compd. | Formula | R |
|---|---|---|
| 3a* | — | — |
| 4a | — | — |
| 5 | IA | —(CH$_2$)$_2$—N⟨piperazine⟩NH |
| 6 | IA | —(CH$_2$)$_3$—N⟨piperazine⟩N—(CH$_2$)$_3$—NH$_2$ |
| 7a | IA | —(CH$_2$)$_2$—C$_6$H$_4$—OH |
| 7b | IA | —(CH$_2$)$_2$—C$_6$H$_3$(OH)—OH |
| 7c | IA | —(CH$_2$)$_2$—C$_6$H$_3$(OCH$_3$)—OCH$_3$ |
| 7d | IA | —CH$_2$CH$_2$OH |
| 7e | IA | H |
| 7f | IA | —CH$_3$ |
| 8a | IB | —(CH$_2$)$_3$—NH—(CH$_2$)$_3$— |
| 8b | IB | —(CH$_2$)$_3$—N(CH$_3$)—(CH$_2$)$_3$— |
| 8c | IB | —(CH$_2$)$_2$—NH—(CH$_2$)$_2$— |
| 9 | IA | —(CH$_2$)$_2$—NH—(CH$_2$)$_2$—OH |
| 10 | IA | —(CH$_2$)$_3$—N(CH$_3$)—(CH$_2$)$_3$—NH$_2$ |

*5H-indolo[3,2-c]quinolin-6-one (compound 3a) as used in the following examples was prepared according to known methods (see, e.g., Yeh-Long Chen et al. (2002), supra).

Synthesis Ex. 1

6-Chloro-11H-indolo[3,2-c]quinoline (4a)

A mixture of compound 3a (1.40 g, 6 mmol) and POCl$_3$ (20 mL) was refluxed for 8 hrs. After cooling, the reaction mixture was poured into ice-H$_2$O (150 mL) and added with concentrated NaOH until a pH of 10 was reached to result in precipitation. The precipitate thus formed was filtered and washed with H$_2$O and then recrystallized with MeOH/DMF to give the title compound 4a (1.44 g, 95% yield).
Detected Properties of the Title Compound:
Mp: 249-250° C. UV $\lambda_{max}$ nm (log ε): 233 (4.43), 264 (4.48), 289 (4.28) in MeOH. IR $\nu_{max}$ (cm$^{-1}$): 1357, 1501, 3199 in KBr. $^1$H-NMR (DMSO-d$_6$) δ: 7.44 (m, 1H), 7.59 (m, 1H), 7.74-7.83 (m, 3H), 8.07 (dd, 1H, J=1.2, 8.4 Hz), 8.45 (d, 1H, J=7.6 Hz), 8.57 (dd, 1H, J=1.6, 8.0 Hz), 13.17 (br s, 1H). $^{13}$C-NMR (DMSO-d$_6$) δ: 55.56, 104.20, 106.71, 111.68, 112.34, 117.42, 118.13, 120.85, 121.01, 124.06, 124.46, 132.35, 137.69, 140.65, 154.16, 159.55. Anal. calcd for C$_{15}$H$_9$ClN$_2$.1.1H$_2$O: C, 66.09; H, 4.14; N, 10.27. found: C, 65.94; H, 4.28; N, 10.34.

Synthesis Ex. 2

N-(11H-Indolo[3,2-c]quinolin-6-yl)-2-(piperazin-1-yl)ethanamine (5)

A mixture of compound 4a as obtained from the above Synthesis Ex. 1 (1.26 g, 5 mmol) and 1-(2-aminoethyl)piperazine (1.94 g, 15 mmol) in 2-ethoxyethanol (50 mL) was heated at 140-150° C. for 48 hrs (by TLC monitoring). After cooling, the reaction mixture was evaporated in vacuo to give a residue, which was dissolved in ethyl acetate (EA) (50 mL). The EA layer was washed with H$_2$O and brine, and then dried on MgSO$_4$. Concentration of the EA layer gave a residue, which was dissolved in MeOH (10 mL), followed by addition of a solution of 6N HCl at 0° C. The resultant mixture was stirred at room temperature for 8 hrs to result in precipitation, followed by filtration. The precipitate thus collected was washed with MeOH and then dried at 90° C. under reduced pressure for 24 hrs to give N-(11H-indolo[3,2-c]quinolin-6-yl)-2-(piperazin-1-yl)ethanamine hydrochloride, which was purified by flash column chromatography (FCC) (silica gel; MeOH/CH$_2$Cl$_2$=1/10 to 1/3) to give the title compound 5 as an orange color powder (0.51 g, 29% yield).
Detected Properties of the Title Compound:
M.p.: 210-211° C. UV $\lambda_{max}$ nm (log ε): 256 (4.61), 296 (4.10), 336 (3.86), 347 (3.85) in MeOH. IR $\nu_{max}$ (cm$^{-1}$): 3402 in KBr. $^1$H-NMR (DMSO-d$_6$) δ: 2.47 (m, 4H, piperazinyl-H), 2.68 (t, 2H, J=6.4 Hz, NHCH$_2$CH$_2$N), 2.77 (m, 4H, piperazinyl-H), 3.77 (m, 2H, NHCH$_2$CH$_2$N), 6.56 (t, 1H, J=4.8 Hz, NH), 7.30 (m, 2H, Ar—H), 7.43 (m, 1H, Ar—H), 7.50 (m, 1H, Ar—H), 7.67 (m, 2H, Ar—H), 8.25 (m, 2H, Ar—H), 12.50 (br s, 1H, NH). $^{13}$C-NMR (200 MHz, DMSO-d$_6$) δ: 37.37, 45.85 (2C), 54.01 (2C), 57.27, 102.70, 111.68, 114.17, 120.02, 120.26, 120.88, 121.38, 121.58, 123.98, 126.28, 128.08, 138.19, 140.69, 146.14, 152.91. Anal. calcd for C$_{21}$H$_{23}$N$_5$.1.0H$_2$O: C, 69.40; H, 6.93; N, 19.27. found: C, 69.68; H, 6.92; N, 19.00.

Synthesis Ex. 3

{3-[4-(3-Aminopropyl)piperazin-1-yl]propyl}(11H-indolo[3,2-c]quinolin-6-yl)amine hydrochloride (6)

The title compound 6 was prepared substantially according to the procedures as set forth in the above Synthesis Ex. 2, except that 1,4-bis(3-aminopropyl)piperazine was used in place of 1-(2-aminoethyl)piperazine. After purification by FCC (MeOH/CH$_2$Cl$_2$=1/10 to 1/3), the title compound 6 was obtained as an orange color powder in a yield of 32%.
Detected Properties of the Title Compound:
M.p.: 87-88° C. UV $\lambda_{max}$ nm (log $\epsilon$): 260 (4.65), 337 (3.84) in MeOH. IR $\nu_{max}$ (cm$^{-1}$): 1621, 1645, 3389 in KBr. $^1$H-NMR (DMSO-d$_6$) δ: 1.63 (quin., 2H, J=6.8 Hz), 1.92 (quin., 2H, J=6.8 Hz), 2.27-2.48 (m, 12H), 2.72 (t, 2H, J=7.2 Hz), 3.40 (br s, 2H, NH$_2$), 3.73 (m, 2H), 6.66 (br s, 1H, NH), 7.29 (m, 2H), 7.42 (m, 1H), 7.49 (m, 1H), 7.65 (m, 2H), 8.27 (dd, 1H, J=1.2, 8.0 Hz), 8.37 (d, 1H, J=8.0 Hz), 12.58 (br s, 1H, NH), 14.05 (br s, 1H, HCl). $^{13}$C-NMR (200 MHz, DMSO-d$_6$) δ: 25.92, 26.03; 38.39, 38.61, 52.51 (2C), 52.93 (2C), 55.06, 56.46, 102.59, 111.33, 114.01, 119.91, 120.59, 120.81, 121.28, 121.51, 123.75, 126.06, 127.88, 137.98, 140.61, 145.98, 152.83. Anal. calcd for C$_{25}$H$_{32}$N$_6$.1.6HCl.1.4H$_2$O: C, 60.04; H, 7.34; N, 16.80. found: C, 59.82; H, 7.42; N, 16.79.

Synthesis Ex. 4

6-[2-(4-Hydroxyphenyl)ethylamino]-11H-indolo[3,2-c]quinoline hydrochloride (7a)

The title compound 7a was prepared substantially according to the procedures as set forth in the above Synthesis Ex. 2, except that 4-(2-aminoethyl)phenol was used in place of 1-(2-aminoethyl)piperazine. After purification by recrystallization with MeOH, the title compound 7a was obtained as a white powder in a yield of 40%.
Detected Properties of the Title Compound:
M.p.: 320-321° C. UV $\lambda_{max}$ nm (log $\epsilon$): 227 (4.50), 256 (4.62), 323 (4.01), 338 (4.12) in MeOH. IR $\nu_{max}$ (cm$^{-1}$): 1610, 1645, 3415 in KBr. $^1$H-NMR (DMSO-d$_6$) δ: 3.03 (t, 2H, J=7.4 Hz), 4.13 (m, 2H), 6.69 (m, 2H), 7.19 (m, 2H), 7.45 (m, 1H), 7.58 (m, 2H), 7.78 (m, 2H), 8.32 (d, 1H, J=8.4 Hz), 8.38 (br s, 1H, NH), 8.52 (m, 2H), 9.29 (br s, 1H, OH), 12.47 (br s, 1H, NH), 13.80 (br s, 1H, HCl). $^{13}$C-NMR (200 MHz, DMSO-d$_6$) δ: 33.69, 43.96, 100.16, 112.74, 113.08, 115.14 (2C), 118.74, 120.73, 121.20, 122.04, 122.79, 124.94, 125.74, 128.39, 129.96 (2C), 130.72, 135.21, 138.56, 141.42, 149.16, 155.93. Anal. calcd for C$_{23}$H$_{19}$N$_3$O.1.0HCl.1.2H$_2$O: C, 67.14; H, 5.49; N, 10.21. found: C, 67.14; H, 5.47; N, 10.20.

Synthesis Ex. 5

6-[2-(3,4-dihydroxyphenyl)ethylamino]-11 indolo[3,2-c]quinoline hydrochloride (7b)

The title compound 7b was prepared substantially according to the procedures as set forth in the above Synthesis Ex. 2, except that 2-(3,4-dihydroxyphenyl)ethylamine was used in place of 1-(2-aminoethyl)piperazine. After purification by FCC (MeOH/CH$_2$Cl$_2$=1/10), followed by recrystallization with MeOH, the title compound 7b was obtained as a white powder in a yield of 15%.
Detected Properties of the Title Compound:
M.p.: 202-203° C. UV $\lambda_{max}$ nm (log $\epsilon$): 241 (4.52), 271 (4.67), 337 (3.99), 350 (4.08) in MeOH. IR $\nu_{max}$ (cm$^{-1}$): 1613, 1647, 3417 in KBr. $^1$H-NMR (DMSO-d$_6$) δ: 2.96 (t, 2H, J=7.4 Hz), 4.08 (m, 2H), 6.66 (m, 2H), 6.80 (d, 1H, J=1.6 Hz), 7.44 (m, 1H), 7.58 (m, 2H), 7.78 (m, 2H), 8.32 (d, 1H, J=7.6 Hz), 8.35 (br s, 1H, NH), 8.50 (d, 1H, J=8.0 Hz), 8.54 (d, 1H, J=8.0 Hz), 8.80 (br s, 1H, OH), 8.84 (br s, 1H, OH), 12.44 (br s, 1H, NH), 13.80 (br s, 1H, HCl). $^{13}$C-NMR (200 MHz, DMSO-d$_6$) δ: 33.88, 43.93, 100.22, 112.66, 112.80, 115.51, 116.45, 118.86, 119.62, 120.74, 121.19, 121.95, 122.78, 124.81, 125.64, 129.14, 130.64, 138.53, 141.37, 143.81, 145.18, 149.24, 155.96. Anal. calcd for C$_{23}$H$_{16}$N$_3$O$_2$.1.0HCl.2.0H$_2$O: C, 62.52; H, 5.47; N, 9.51. found: C, 62.58; H, 5.45; N, 9.63.

Synthesis Ex. 6

6-[2-(3,4-dimethoxyphenyl)ethylamino]-11H-indolo[3,2-c]quinoline hydrochloride (7c)

The title compound 7c was prepared substantially according to the procedures as set forth in the above Synthesis Ex. 2, except that 2-(3,4-dimethoxyphenyl)ethylamine was used in place of 1-(2-aminoethyl)piperazine. After purification by recrystallization with MeOH, the title compound 7c was obtained as a white powder in a yield of 66%.
Detected Properties of the Title Compound:
M.p.: 231-232° C. UV $\lambda_{max}$ nm (log $\epsilon$): 229 (4.40), 258 (4.69), 323 (3.96), 338 (4.08) in MeOH. IR $\nu_{max}$ (cm$^{-1}$): 1645, 1612, 3411 in KBr. $^1$H-NMR (DMSO-d$_6$) δ: 3.07 (t, 2H, J=7.4 Hz), 3.01 (s, 3H), 3.65 (s, 3H), 4.23 (m, 2H), 6.78 (d, 1H, J=8.0 Hz), 6.86 (dd, 1H, J=1.6, 8.0 Hz), 7.05 (d, 1H, J=1.6 Hz), 7.44 (m, 1H), 7.55 (m, 2H), 7.77 (m, 2H), 8.34 (br s, 1H, NH), 8.38 (d, 1H, J=8.0 Hz), 8.52 (m, 2H), 12.60 (br s, 1H, NH), 13.80 (br s, 1H, HCl). $^{13}$C-NMR (200 MHz, DMSO-d$_6$) δ: 34.32, 43.89, 55.28, 55.49, 100.14, 111.88, 112.66, 112.70, 113.06, 118.74, 120.68, 120.98, 121.18, 121.97, 122.72, 124.84, 125.71, 130.61, 130.86, 135.24, 138.53, 141.38, 147.37, 148.58, 149.21. Anal. calcd for C$_{26}$H$_{23}$N$_3$O$_2$.1.0HCl.1.2H$_2$O: C, 65.92; H, 5.84; N, 9.22. found: C, 65.89; H, 5.93; N, 9.29.

Synthesis Ex. 7

2-(11H-indolo[3,2-c]quinolin-6-ylamino)ethanol hydrochloride (7d)

A mixture of compound 4a as obtained from the above Synthesis Ex. 1 (0.50 g, 2 mmol) and 2-aminoethanol (0.24 g, 4 mmol) in 2-ethoxyethanol (20 mL) was heated at 140-150° C. for 48 hrs (by TLC monitoring). After cooling, the reaction mixture was evaporated in vacuo to give a residue, which was treated with MeOH (30 mL) to result in precipitation. The resultant precipitate was collected by filtration and recrystallized with MeOH to give the title compound 7d as a white powder (0.38 g, 61% yield).
Detected Properties of the Title Compound:
M.p.: 344-345° C. UV $\lambda_{max}$ nm (log $\epsilon$): 240 (4.48), 263 (4.59), 322 (4.02), 336 (4.11), 350 (4.22) in MeOH. IR $\nu_{max}$ (cm$^{-1}$): 1647, 3383 in KBr. $^1$H-NMR (DMSO-d$_6$+TFA-d) δ: 3.88 (t, 2H, J=4.8 Hz), 4.02 (t, 2H, J=4.8 Hz), 7.46 (m, 1H), 7.60 (m, 2H), 7.76-7.81 (m, 2H), 8.18 (d, 1H, J=8.4 Hz), 8.38 (br s, 1H, NH), 8.48 (m, 1H), 8.58 (d, 1H, J=8.0 Hz), 12.38 (br s, 1H, NH), 13.59 (br s, 1H, HCl). $^{13}$C-NMR (DMSO-d$_6$) δ: 45.19, 60.22, 100.64, 112.97, 113.04, 118.83, 121.06, 121.64, 122.39, 123.05, 125.25, 126.05, 131.11, 138.77, 138.94, 141.61, 141.78. Anal. calcd for C$_{17}$H$_{15}$N$_3$O.HCl: C, 65.08; H, 5.14; N, 13.39. found: C, 65.02; H, 5.22; N, 13.36.

Synthesis Ex. 8

11H-Indolo[3,2-c]quinolin-6-ylamine hydrochloride (7e)

A mixture of compound 4a as obtained from the above Synthesis Ex. 1 (0.50 g, 2 mmol) and 29% ammonium hydroxide (20 mL) was heated in a sealed steel bomb at 120-130° C. for 48 hrs (by TLC monitoring). The reaction mixture was evaporated under reduced pressure, followed by addition of H$_2$O (100 mL). The resultant precipitate was collected, washed with H$_2$O, and purified by FCC (silica gel; MeOH/CH$_2$Cl$_2$=1/5) to give the title compound 7e as a brown powder (0.17 g, 54% yield).

Detected Properties of the Title Compound:

M.p.: 377-378° C. UV $\lambda^{max}$ nm (log ε): 225 (4.35), 249 (4.45), 292 (4.04), 322 (3.04), 336 (4.15) in MeOH. IR $v_{max}$ (cm$^{-1}$): 1650, 3304, 3394 in KBr. $^1$H-NMR (DMSO-d$_6$) δ: 7.41 (m, 1H), 7.53 (m, 2H), 7.71-7.79 (m, 3H), 8.23 (br s, 2H, NH$_2$), 8.51 (m, 2H), 10.28 (br s, 1H, NH), 13.60 (br s, 1H, NH). $^{13}$C-NMR (DMSO-d$_6$) δ: 100.38, 112.47, 112.67, 119.07, 120.84, 121.52, 121.85, 122.84, 124.04, 125.49, 130.58, 136.46, 138.54, 142.01, 151.18. Anal. calcd for C$_{15}$H$_{11}$N$_3$·HCl·1.2H$_2$O: C, 61.84; H, 4.98; N, 14.42. found: C, 61.83; H, 4.95; N, 14.33.

Synthesis Ex. 9

N-Methyl-11H-indolo[3,2-c]quinolin-6-ylamine (7f)

The title compound 7f was prepared substantially according to the procedures as set forth in the above Synthesis Ex. 8, except that 40% methylamine (30 mL) was used in place of 29% ammonium hydroxide (20 mL). After purification by FCC (MeOH/CH$_2$Cl$_2$=1/50), the title compound 7f was obtained as a yellow powder in a yield of 85%.

Detected Properties of the Title Compound:

M.p.: 146-147° C. UV $\lambda_{max}$ nm (log ε): 254 (4.46), 295 (3.98), 336 (3.87), 349 (3.74) in MeOH. $^1$H-NMR (DMSO-d$_6$) δ: 3.18 (d, 3H, J=4.4 Hz, CH$_3$), 6.78 (br s, 1H, NH), 7.31 (m, 2H), 7.43 (m, 1H), 7.53 (m, 1H), 7.66 (d, 1H, J=8.4 Hz), 7.73 (d, 1H, J=8.0 Hz), 8.27 (dd, 1H, J=1.2, 8.0 Hz), 8.42 (d, 1H, J=8.4 Hz), 12.55 (br s, 1H, NH). $^{13}$C-NMR (200 MHz, DMSO-d$_6$) δ: 28.37, 102.67, 111.50, 114.06, 120.21, 120.65, 121.01, 121.45, 121.62, 124.00, 125.80, 128.19, 138.12, 140.65, 145.52, 153.31. Anal. calcd for C$_{16}$H$_{13}$N$_3$·0.6H$_2$O: C, 74.46; H, 5.54; N, 16.28. found: C, 74.46; H, 5.53; N, 16.13.

Synthesis Ex. 10

N,N-bis-[3-(11H-indolo[3,2-c]quinolin-6-yl)aminopropyl]amine hydrochloride (8a)

A mixture of compound 4a as obtained from the above Synthesis Ex. 1 (1.26 g, 5 mmol), dipropylenetriamine (1.31 g, 10 mmol), pyridine (0.8 mL) and ethoxyethanol (20 mL) was heated in a sealed steel bomb at 100-120° C. for 4 days (by TLC monitoring). After cooling, the reaction mixture was evaporated in vacuo to give a residue, which was subsequently treated with 1N HCl (30 mL). The resultant mixture was stirred at room temperature overnight, followed by filtration. The filtrate thus collected was added with solid NaHCO$_3$ to neutralize HCl. The resultant precipitate was collected by filtration and purified by FCC (MeOH/CH$_2$Cl$_2$=1/5), followed by recrystallization with EtOH, giving the title compound 8a as a white powder (0.45 g, 16% yield).

Detected Properties of the Title Compound:

M.p.: 107-108° C. UV $\lambda_{max}$ nm (log ε): 242 (4.68), 267 (4.84), 350 (4.26) in MeOH. IR $v_{max}$ (cm$^{-1}$): 1612, 1645, 3384 in KBr. $^1$H-NMR (DMSO-d$_6$) δ: 2.21 (m, 4H), 3.16 (m, 4H), 4.16 (m, 4H), 7.38 (m, 2H), 7.51 (m, 2H), 7.57 (m, 2H), 7.70-7.78 (m, 4H), 8.52 (m, 4H), 8.75 (m, 2H), 9.41 (br s, 2H), 12.71 (br s, 2H), 13.84 (br s, 2H, HCl). $^{13}$C-NMR (200 MHz, DMSO-d$_6$) δ: 25.37, 42.46, 44.18, 100.39, 112.60, 112.88, 118.94, 121.02, 121.24, 121.96, 122.72, 124.87, 125.63, 130.52, 135.48, 138.52, 141.44, 149.22. Anal. calcd for C$_{36}$H$_{33}$N$_7$·2.4HCl·3.0H$_2$O: C, 61.31; H, 5.92; N, 13.90. found: C, 61.33; H, 5.72; N, 13.83.

Synthesis Ex. 11

N,N-bis-[3-(11H-indolo[3,2-c]quinolin-6-yl)aminopropyl]-N-methylamine hydrochloride (8b)

The title compound 8b was prepared substantially according to the procedures as set forth in the above Synthesis Ex. 10, except that N,N-bis(3-aminopropyl)methylamine was used in place of dipropylenetriamine. After purification by recrystallization with EtOH, the title compound 8b was obtained as a white powder in a yield of 21%.

Detected Properties of the Title Compound:

M.p.: 76-77° C. UV $\lambda_{max}$ nm (log ε): 259 (4.59), 337 (3.79) in MeOH. IR $\lambda_{max}$ (cm$^{-1}$): 1614, 1650, 3398 in KBr. $^1$H-NMR (DMSO-d$_6$) δ: 2.31 (m, 4H), 2.89 (s, 3H), 3.35-3.49 (m, 4H), 4.11 (m, 4H), 7.39 (m, 2H, Ar—H), 7.51 (m, 2H, Ar—H), 7.61 (m, 2H, Ar—H), 7.71-7.78 (m, 4H, Ar—H), 8.45-8.50 (m, 4H, Ar—H), 8.55 (br s, 2H, NH), 8.66 (m, 2H, Ar—H), 10.60 (br s, 1H, NH), 12.71 (br s, 1H, NH), 13.64 (br s, 1H, HCl). $^{13}$C-NMR (200 MHz, DMSO-d$_6$) δ: 23.42, 40.21, 42.06, 52.19, 100.24, 112.49, 112.82, 118.88, 120.86, 121.15, 121.81, 122.65, 124.72, 125.48, 130.32, 135.40, 138.44, 141.36, 149.13. Anal. calcd for C$_{37}$H$_{35}$N$_7$·1.2HCl·0.9H$_2$O: C, 70.30; H, 6.11; N, 15.51. found: C, 70.34; H, 6.04; N, 15.42.

Synthesis Ex. 12

N,N-bis-[3-(11H-indolo[3,2-c]quinolin-6-yl)aminoethyl]amine hydrochloride (8c)

A mixture of compound 4a as obtained from the above Synthesis Ex. 1 (1.26 g, 5 mmol), diethylenetriamine (1.03 g, 10 mmol), pyridine (0.8 mL) and ethoxyethanol (20 mL) was heated in a sealed steel bomb at 100-120° C. for 3 days (by TLC monitoring). After cooling, the reaction mixture was evaporated in vacuo to give a residue, which was subsequently treated with 1N HCl (30 mL). The resultant mixture was stirred at room temperature overnight, followed by filtration. The filtrate thus collected was added with solid NaHCO$_3$ to neutralize HCl. The resultant precipitate was collected by filtration and purified by FCC (MeOH/CH$_2$Cl$_2$=1/3), followed by recrystallization with EtOH, giving the title compound 8c (0.91 g, 34% yield).

Detected Properties of the Title Compound:

M.p.: 202-203° C. UV $\lambda_{max}$ nm (log ε): 243 (4.62), 269 (4.05), 348 (3.89) in MeOH. IR $v_{max}$ (cm$^{-1}$): 1615, 1647, 3351 in KBr. $^1$H-NMR (DMSO-d$_6$) δ: 3.07 (t, 4H, J=6.0 Hz), 3.60 (br s, 3H), 3.85 (t, 4H, J=6.0 Hz), 6.83 (br s, 2H), 7.30 (m, 4H), 7.42 (m, 2H), 7.51 (m, 2H), 7.68 (m, 4H), 8.32 (dd, 2H, J=1.2, 8.0 Hz), 8.41 (d, 2H, J=8.0 Hz), 12.64 (br s, 2H, HCl).

$^{13}$C-NMR (200 MHz, DMSO-$d_6$) δ: 39.66, 45.94, 102.69, 111.49, 114.21, 120.10, 120.80, 121.03, 121.32, 121.76, 123.96, 126.02, 128.10, 138.13, 140.81, 145.64, 152.94. Anal. calcd for $C_{34}H_{29}N_7$.2.0HCl.0.5H$_2$O: C, 66.13; H, 5.22; N, 15.88. found: C, 66.08; H, 5.44; N, 16.16.

Synthesis Ex. 13

2-[2-(11H-Indolo[3,2-c]quinolin-6-ylamino)ethylamino]ethanol hydrochloride (9)

A mixture of compound 4a as obtained from the above Synthesis Ex. 1 (0.50 g, 2 mmol) and N-(2-hydroxyethyl)ethylenediamine (0.63 g, 6 mmol) in 2-ethoxyethanol (5 mL) was heated at 140-150° C. for 24 hrs (by TLC monitoring). After cooling, the reaction mixture was evaporated in vacuo to give a residue, which was dissolved in EA (50 mL). The EA layer was washed with H$_2$O and brine and then dried (MgSO$_4$). Concentration of the EA layer gave a residue, which was dissolved in MeOH (10 mL) and then added with a solution of 6N HCl at 0° C., followed by stirring at room temperature for 8 hrs. The resultant precipitate was filtered off, washed with MeOH, and dried at 90° C. under reduced pressure for 24 hrs to give the title compound 9 (0.50 g, 70% yield).

Detected Properties of the Title Compound:

M.p.: 276° C. UV $\lambda_{max}$ nm (log ε): 230 (4.31), 264 (4.66), 295 (3.98), 308 (3.73), 329 (3.74), 343 (3.81) in MeOH. IR $\nu_{max}$ (cm$^{-1}$): 1644, 3321 in KBr. $^1$H-NMR (DMSO-$d_6$) δ: 3.15 (m, 2H), 3.40 (m, 2H), 3.73 (t, 2H, J=5.6 Hz), 4.45 (m, 2H), 7.43 (t, 1H, J=7.6 Hz), 7.53-7.65 (m, 2H), 7.79 (m, 2H), 8.61 (m, 2H), 8.70-8.76 (m, 2H), 9.25 (br s, 2H), 13.05 (br s, 1H, NH), 13.97 (br s, 1H, HCl). $^{13}$C-NMR (DMSO-$d_6$) δ: 45.79, 49.19, 56.34 (2C), 100.41, 112.50, 112.75, 118.82, 121.14, 121.18, 121.79, 122.73, 124.96, 125.63, 130.44, 135.20, 138.43, 141.36, 149.19. Anal. calcd for $C_{19}H_{21}ClN_4$O.0.6H$_2$O: C, 62.07; H, 6.09; N, 15.24. found: C, 62.96; H, 6.18; N, 15.28.

Synthesis Ex. 14

N$^1$-[3-(11H-Indolo[3,2-c]quinolin-6-ylamino)propyl]-N$^1$-methylpropane-1,3-diamine hydrochloride (10)

The title compound 10 was prepared substantially according to the procedures as set forth in the above Synthesis Ex. 13, except that N$^1$-(3-aminopropyl)-N$^1$-methylpropane-1,3-diamine was used in place of N-(2-hydroxyethyl)ethylenediamine. After purification by FCC (MeOH/CH$_2$Cl$_2$=1/3), the title compound 10 was obtained as a brown powder in a yield of 43%.

Detected Properties of the Title Compound:

M.p.: 76-77° C. UV $\lambda_{max}$ nm (log ε): 259 (4.59), 336 (3.79), 347 (3.83) in MeOH. IR $\nu_{max}$ (cm$^{-1}$): 1614, 3398 in KBr. $^1$H-NMR (DMSO-$d_6$) δ: 1.82 (quin., 2H, J=7.2 Hz), 1.98 (quin., 2H, J=6.8 Hz), 2.34 (s, 3H), 2.60 (m, 4H), 2.84 (t, 2H, J=7.2 Hz), 3.41 (br s, 2H, NH$_2$), 3.75 (t, 2H, J=6.8 Hz), 6.85 (br s, 1H, NH), 7.28 (m, 2H), 7.41 (m, 1H), 7.50 (m, 1H), 7.67 (m, 2H), 8.30 (dd, 1H, J=1.2, 8.0 Hz), 8.37 (d, 1H, J=8.0 Hz), 12.62 (br s, 1H, NH), 13.94 (br s, 1H, HCl). $^{13}$C-NMR (200 MHz, DMSO-$d_6$) δ: 23.81, 26.03, 37.39, 37.42, 41.14, 53.94, 55.13, 102.61, 111.48, 114.12, 120.08, 120.54, 120.81, 121.37, 121.72, 123.87, 126.00, 128.05, 138.11, 140.74, 145.82, 152.82. Anal. calcd for $C_{22}H_{27}N_5$.1.0HCl.1.2H$_2$O: C, 62.98; H, 7.30; N, 16.69. found: C, 62.70; H, 7.65; N, 16.85.

Pharmacological Examples

In order to determine the biological activities of the compounds of formula (I) according to this invention, the following assays were performed.

In Vitro Anticancer Assay

Selected compounds were evaluated in vitro against the NCI's full panel of 60 cancer cell lines derived from nine cancer cell types, including: leukemia (CCRF-CEM, HL-60 (TB), K-562, MOLT-4, RPMI-8226, and SR); non-small cell lung cancer (A549/ATCC, EKVX, HOP-62, HOP-92, NCI-H226, NCI-H23, NCI-H322M, and NCI-H522); colon cancer (COLO 205, HCC-2998, HCT-116, HCT-15, HT29, KM12, and SW-620); CNS cancer (SF-268, SF-295, SF-539, SNB-19, SNB-75, and U251); melanoma (LOX IMVI, MALME-3M, M14, SK-MEL-2, SK-MEL-28, SK-MEL-5, UACC-62, and UACC-257); ovarian cancer (IGROV1, OVCAR-3, OVCAR-4, OVCAR-5, OVCAR-8, and SK-OV-3); renal cancer (786-0, A498, ACHN, CAKI-1, RXF 393, SN12C, TK-10, and UO-31); prostate cancer (PC-3 and DU-145); and breast cancer (MCF7, MCF7/ADR-RES, MDA-MB-231/ATCC, HS 578T, MDA-MB-435, MDA-N, and T-47D). For each compound, dose-response curves for each cell line were measured with five different drug concentrations, and the concentration causing 50% cell growth inhibition (GI$_{50}$) compared with the control was calculated. The mean GI$_{50}$ values of each tested compound for all the 60 tumor cell lines were also calculated. The obtained results were summarized in Table 2.

TABLE 2

Anticancer activities of selected compounds against representative cancer cell lines (GI$_{50}$: μM$^a$)

| | 5 | 6 | 7a | 7d | 7e | 8a | 8b | 9 | 10 |
|---|---|---|---|---|---|---|---|---|---|
| Leukemia | | | | | | | | | |
| HL-60 (TB) | 0.29 | 0.42 | 2.40 | 0.56 | 1.98 | 0.04 | <0.01 | 1.31 | 0.09 |
| K-562 | 0.07 | 0.07 | 1.91 | 0.46 | 0.62 | 0.04 | <0.01 | 1.55 | 0.04 |
| SR | 0.18 | 0.35 | 1.48 | 0.21 | 0.64 | 0.03 | <0.01 | 0.90 | 0.37 |
| Non-small cell lung cancer | | | | | | | | | |
| A549/ATCC | 0.11 | 0.20 | 1.33 | 0.41 | 1.09 | 0.06 | <0.01 | 0.98 | 0.08 |
| HOP-62 | 0.40 | 0.24 | 1.63 | 0.58 | 1.13 | 0.05 | <0.01 | 0.37 | 0.15 |
| NCI-H460 | 0.19 | 0.30 | 1.31 | 0.29 | 0.41 | 0.04 | <0.01 | 1.46 | 0.31 |
| Colon cancer | | | | | | | | | |
| COLO 205 | 0.22 | 0.21 | 1.18 | 0.31 | 1.07 | 0.18 | 0.02 | 1.76 | 0.18 |
| HCT-116 | 0.07 | 0.18 | 1.22 | 0.23 | 0.50 | 0.17 | <0.01 | 0.19 | 0.08 |

TABLE 2-continued

Anticancer activities of selected compounds against representative cancer cell lines (GI$_{50}$: μM$^a$)

| | 5 | 6 | 7a | 7d | 7e | 8a | 8b | 9 | 10 |
|---|---|---|---|---|---|---|---|---|---|
| HT29 | 0.12 | 0.14 | 1.42 | 0.28 | 0.51 | 0.05 | <0.01 | 0.56 | 0.15 |
| CNS cancer | | | | | | | | | |
| SF-268 | 0.50 | 0.31 | 1.71 | 0.56 | 1.97 | 0.03 | <0.01 | 1.36 | 0.25 |
| SF-295 | 0.31 | 0.14 | 1.38 | 0.45 | 1.03 | 0.10 | <0.01 | 1.41 | 0.13 |
| SNB-19 | 0.30 | 0.27 | 1.83 | 0.41 | 1.10 | 0.07 | <0.01 | 2.10 | 0.15 |
| Melanoma | | | | | | | | | |
| LOX IMVI | 0.20 | 0.29 | 1.59 | 0.36 | 1.05 | 0.07 | <0.01 | 0.44 | 0.21 |
| SK-MEL-2 | 1.06 | 0.18 | 1.73 | 0.57 | 1.54 | 0.55 | 0.07 | 2.25 | 0.20 |
| UACC-62 | 1.26 | 0.21 | 1.66 | 1.15 | 13.5 | 0.22 | 0.06 | 2.00 | 0.19 |
| Ovarian cancer | | | | | | | | | |
| OVCAR-3 | 0.27 | 0.24 | 1.60 | 0.47 | 1.42 | 0.52 | 0.05 | 1.31 | 0.22 |
| OVCAR-5 | 0.54 | 0.25 | 2.89 | 1.03 | 1.84 | 0.22 | 0.08 | 0.58 | 0.15 |
| OVCAR-8 | 0.04 | 0.04 | 1.02 | 0.36 | 0.98 | 0.04 | <0.01 | 0.81 | 0.04 |
| Renal cancer | | | | | | | | | |
| 786-0 | 0.22 | 0.26 | 1.29 | 0.45 | 1.12 | 0.07 | <0.01 | 0.34 | 0.09 |
| ACHN | 0.38 | 0.20 | 1.27 | 0.16 | 0.48 | 0.06 | 0.02 | 0.38 | 0.38 |
| SN12C | 0.08 | <0.01 | 1.27 | 0.22 | 1.24 | 0.03 | <0.01 | 1.26 | 0.07 |
| Prostate cancer | | | | | | | | | |
| PC-3 | 0.31 | 0.35 | 1.63 | nd$^b$ | nd$^b$ | 0.36 | 0.07 | 0.88 | 0.32 |
| DU-145 | 0.16 | 0.12 | 1.45 | 0.69 | 1.94 | 0.13 | 0.05 | 0.74 | 0.24 |
| Breast cancer | | | | | | | | | |
| MCF7 | 0.08 | 0.12 | 1.37 | 0.37 | 1.19 | 0.01 | <0.01 | 1.24 | 0.05 |
| MDA-MB-231/ATCC | 0.34 | 0.23 | 1.36 | 0.43 | 1.22 | 0.18 | 0.09 | 1.24 | 0.17 |
| MDA-MB-435 | 0.63 | 0.37 | 1.60 | 0.41 | 0.94 | 0.85 | 0.11 | 1.46 | 0.19 |
| MG MID$^c$ | 0.35 | 0.30 | 1.70 | 0.46 | 1.29 | 0.15 | <0.02 | 1.07 | 0.18 |

$^a$GI$_{50}$: Drug molar concentration causing 50% cell growth inhibition.
$^b$nd, not determined.
$^c$Mean values of over all cell lines tested.

Referring to Table 2, unexpectedly, compound 8b has a GI$_{50}$ value ranging from less than 0.01 μM to about 0.11 μM for each cell line (a mean GI$_{50}$ value of less than 0.02 μM); compound 8a has a mean GI$_{50}$ value of 0.15 μM; compound 10 has a mean GI$_{50}$ value of 0.18 μM; compounds 5 and 6 each have a mean GI$_{50}$ value of about 0.30 μM; and the mean GI$_{50}$ values of compounds 7d, 9, 7e and 7a are 0.46 μM, 1.07 μM, 1.29 μM and 1.70 μM, respectively.

The compounds of formula (I) according to this invention are shown to have a broad and potent anticancer activity. It is thus contemplated that compounds of formula (I) of this invention can be used for the treatment of cancer diseases, especially leukemia, non-small cell lung cancer, colon cancer, CNS cancer, melanoma, ovarian cancer, renal cancer, prostate cancer, and breast cancer.

Telomeric Repeat Amplification Protocol (TRAP) assay

The inhibition of telomerase activity in a cell-free assay by selected compounds was assessed using a TRAP assay (N W Kim et al. (1994), *Science*, 266:2011-2015) with minor modification.

Briefly, total cell extracts were prepared from exponentially growing H1299 human lung cancer cells. The cultured H1299 cells were trypsinized, washed with PBS, and then resuspended in lysis buffer containing 10 mM Tris-HCl (pH 7.5), 1 mM MgCl$_2$, 1 mM EGTA, 10% glycerol, 5 mM β-mercaptoethanol, 0.1 mM phenylmethylsulfonyl fluoride (PMSF) and 0.5% 3-[(3-cholamidopropyl)dimethylammonio]-1-propanesulfonate (CHAPS) and extracted for 30 min at 4° C. After centrifugation at 20,000 g, the supernatant thus obtained was divided into aliquots and frozen. The protein concentration was determined by Bradford assay.

In the presence or absence of a test compound, 0.5 μg of total cell extract as prepared above was incubated with a 40 μL reaction buffer containing TRAP buffer (20 mM Tris-HCl, pH 8.3), 68 mM KCl, 1.5 mM MgCl$_2$, 1 mM EGTA, 0.05% v/v Tween 20), 50 μM of each deoxynucleotide triphosphate, and 0.1 μg of forward TS primer (5'-aatccgtcgagcagagtt-3', SEQ ID NO:1) for 30 min at 25° C. RNase A was mixed with the cell extract before the incubation in a control. Telomerase activity was then inactivated at 94° C. in a PCR block of a thermal cycler for 5 min. 0.1 μg of reverse CX primer (5'-ccttacccttacccttacccctaa-3', SEQ ID NO:2) and 2 units of Taq DNA polymerase were added. A three-step PCR was then performed as follows: 94° C. for 30 s, 55° C. for 30 s, and 72° C. for 1 min, running for 33 cycles. The telomerase-extended PCR products were resolved by 10% polyacrylamide gel electrophoresis and visualized by staining with SYBER Green.

Referring to FIG. 1, compounds 5, 6, 8a and 8b completely inhibited telomerase activity at approximately 0.02 nM. Compounds 7a, 7b, and 7c were also effective and completely inhibited telomerase activity at approximately 2 nM.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

We claim:

1. A compound of formula (I):

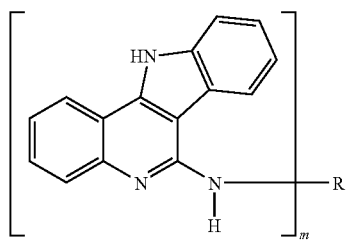

(I)

or a pharmaceutically acceptable salt thereof,
wherein:
m is an integer selected from 1 and 2;
when m is 1, R represents a monovalent group selected from the group consisting of:

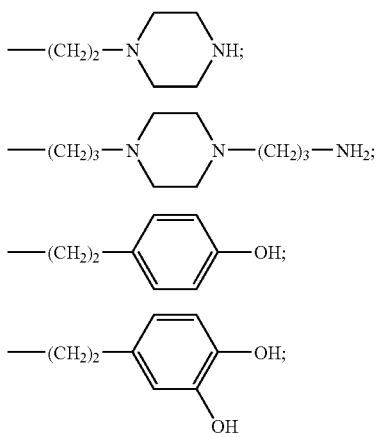

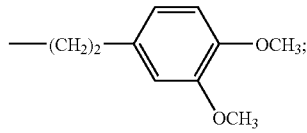

(v)

(vi) —CH$_2$CH$_2$OH;
(vii) —(CH$_2$)$_2$—NH—(CH$_2$)$_2$—OH;
(viii) —(CH$_2$)$_3$—N(CH$_3$)—(CH$_2$)$_3$—NH$_2$;
(ix) H; and
(x) —CH$_3$; and
when m is 2, R is a divalent group represented by the formula —(CH$_2$)$_n$—N(R')—(CH$_2$)$_n$—, wherein R' is selected from hydrogen and methyl and n is an integer from 2 to 4.

2. The compound of claim 1, wherein m is 1.

3. The compound of claim 2, which is selected from:
N-(11H-Indolo[3,2-c]quinolin-6-yl)-2-(piperazin-1-yl)ethanamine;
{3-[4-(3-aminopropyl)piperazin-1-yl]propyl}(11H-indolo[3,2-c]quinolin-6-yl)amine hydrochloride;
6-[2-(4-Hydroxyphenyl)ethylamino]-11H-indolo[3,2-c]quinoline hydrochloride;
6-[2-(3,4-dihydroxyphenyl)ethylamino]-11H-indolo[3,2-c]quinoline hydrochloride;
6-[2-(3,4-dimethoxyphenyl)ethylamino]-11H-indolo[3,2-d]quinoline hydrochloride;
2-(11H-indolo[3,2-d]quinolin-6-ylamino)ethanol hydrochloride;
11H-Indolo[3,2-c]quinolin-6-ylamine hydrochloride;
2-[2-(11H-Indolo[3,2-c]quinolin-6-ylamino)ethylamino]ethanol hydrochloride; and
N$^1$-[3-(11H-indolo[3,2-c]quinolin-6-ylamino)propyl]-N$^1$-methylpropane-1,3-diamine hydrochloride.

4. The compound of claim 1, wherein m is 2.

5. The compound of claim 4, which is selected from:
N,N-bis-[3-(11H-indolo[3,2-c]quinolin-6-yl)aminopropyl]amine hydrochloride; and N,N-bis-[3-(11H-indolo[3,2-c]quinolin-6-yl)aminopropyl]-N-methylamine hydrochloride.

6. A pharmaceutical composition, comprising a compound of claim 1.

7. A method for inhibiting DNA replication or transcription in a tumor cell, comprising contacting the tumor cell with a compound of claim 1, wherein the tumor cell is one derived from a cancer selected from leukemia, non-small cell lung cancer, colon cancer, CNS cancer, melanoma, ovarian cancer, renal cancer, prostate cancer, and breast cancer.

8. A method for treating a cancer, comprising administering to a subject in need thereof a compound of claim 1, wherein the cancer is selected from leukemia, non-small cell lung cancer, colon cancer, CNS cancer, melanoma, ovarian cancer, renal cancer, prostate cancer, and breast cancer.

* * * * *

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: PCR Primer

<400> SEQUENCE: 1
aatccgtcga gcagagtt                                                 18

<210> SEQ ID NO 2
<211> LENGTH: 24
<212> TYPE: DNA
<213> ORGANISM: Artificial Sequence
<220> FEATURE:
<223> OTHER INFORMATION: PCR Primer

<400> SEQUENCE: 2
cccttaccct taccttacc ctaa                                           24